United States Patent

Guillaumet et al.

Patent Number: 5,084,456
Date of Patent: Jan. 28, 1992

[54] OXAZOLOPYRIDINE COMPOUNDS

[75] Inventors: Gérald Guillaumet; Christine Flouzat; Jacqueline Bonnet, all of Orleans, France

[73] Assignee: Science et Organisation, Neuilly-sur-Seine, France

[21] Appl. No.: 564,035

[22] Filed: Aug. 7, 1990

[30] Foreign Application Priority Data

Aug. 7, 1989 [FR] France .................. 89 10597

[51] Int. Cl.$^5$ .................. C07D 401/12; C07D 401/14; A61K 31/495
[52] U.S. Cl. .................. 514/252; 514/253; 514/254; 544/295; 544/360; 544/362; 544/363; 544/364
[58] Field of Search .................. 544/295, 360, 362, 363, 544/364; 514/252, 253, 254

[56] References Cited

U.S. PATENT DOCUMENTS 4,038,396  7/1977  Shen et al. .................. 546/116

FOREIGN PATENT DOCUMENTS 63-146872A  6/1988  Japan.

Primary Examiner—John M. Ford
Assistant Examiner—Jyothsna Venkat
Attorney, Agent, or Firm—Gordon W. Hueschen

[57] ABSTRACT

Compounds of general formula (I):

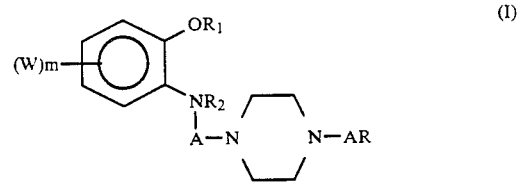

in which:

$R_1$ and $R_2$ each represent a hydrogen atom or, with the oxygen and nitrogen, form an —O—CO—N— linkage, W represents a halogen atom or a lower alkyl or alkoxy group optionally substituted with one or more halogen atoms, such as trifluoromethyl, and m being between 0 and 3, A represents a linear or branched lower alkylene group, and Ar represents an aryl or heteroaryl group optionally substituted with one or more halogen atoms or with one or more lower alkyl, hydroxy, hydroxysulfonyloxy, lower alkoxy or aryloxy groups optionally substituted with one or more halogen atoms, such as a trifluoromethyl group, on the understanding that lower alkyl or lower alkyloxy radical is understood to mean a linear or branched alkyl group comprising from 1 to 6 carbon atom, their isomers, epimers and diastereoisomers. Medicinal products useful in the treatment of pain.

15 Claims, No Drawings

OXAZOLOPYRIDINE COMPOUNDS

The present invention relates to new oxazolo [4,5-b]pyridine compounds, to a process for preparing these and to pharmaceutical compositions containing them.

The properties, both analgesic and anti-inflammatory, of 2-phenyloxazolo[5,4- or -[4,5]pyridines are already known (Patents U.S. Pat. No. 4,038,396, FR 2,328,471, FR 2,319,354, GB 1,421,619).

However, these products possess an essentially anti-inflammatory profile, as confirmed by the therapeutic indications mentioned in the patents cited above, or else have the drawback of not dissociating the two types of activity: analgesic on the one hand, antipyretic and anti-inflammatory on the other hand.

The applicant has now discovered new compounds whose level of analgesic activity is at least comparable, or even superior, to that of the already known 2-phenyl-3H-oxazolo[4,5-b]pyridines, but possessing the especially advantageous feature of being completely devoid of anti-inflammatory activity: the compounds of the present invention are, in effect, endowed with a high-level pure analgesic activity. In point of fact, most non-morphinic analgesic substances known to date also possess anti-inflammatory activity (for example salicyl compounds, pyrazole compounds, etc.), and they consequently intervene in the processes occurring in inflammation. These processes involve a very large number of chemical mediators (prostaglandins, thomboxane A2, etc.); multi-farious sides effects accordingly ensue, the base known of which are: attack of the gastric mucosa with the possibility of ulcers, and inhibition of platelet aggregation with disorders of coagulation. Apart from the disturbances they cause, these concomitant effects prohibit the use of these products in many subjects who are especially sensitve to them. Being devoid of all anti-inflammatory activity, the compounds of the present invention hence do not interact with the mediators of inflammation, and are hence avoid of the side effects mentioned above. This feature, combined with their complete absence of toxicity and their high level of activity, renders the compounds of the present invention usable as an analgesic much more safely and without the restrictions in use customarily known for the large majority of these products.

More specifically, the invention relates to compounds of general formula (I):

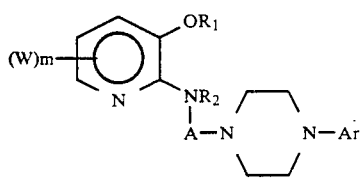

in which:
R$_1$ and R$_2$ each represent a hydrogen atom or, with the oxygen and nitrogen which bear them, form an —O—CO—N—linkage, W represents a halogen atom or a lower alkyl or alkoxy group optionally substituted with one or more halogen atoms, such as trifluoromethyl, m being between 0 and 3, A represents a linear or branched lower alkylene group, and Ar represents an aryl or heteroaryl group optionally substituted with one or more halogen atoms or with one or more lower alkyl, hydroxy, hydroxysulfonyloxy, lower alkoxy or aryloxy groups optionally substituted with one or more halogen atoms, such as a trifluoromethyl group, on the understanding that lower alkyl or lower alkyloxy radical is understood to mean a linear or branched alkyl group comprising from 1 to 6 carbon atoms, and that aryl or heteroaryl groups are understood to mean unsaturated mono- or bicyclic groups comprising from 5 to 12 atoms incorporating or otherwise one, two or three hetero atoms selected from nitrogen, oxygen or sulfur in their carbon skeleton, their isomers, and also their addition salts with a pharmaceutically acceptable acid and, when R$_1$ and R$_2$ each represent a hydrocarbon atom, their addition salts with a pharmaceutically acceptable base.

Among acids which may be added to the compounds of formula (I) to form an addition salt, hydrochloric, sulfuric, phosphoric, tartaric, malic, maleic, fumaric, oxalic, methanesulfonic, ethanesulfonic, camphoric and citric acids, etc., may be mentioned by way of example.

Among the compounds of the invention, preference is at present give to those for which:

Ar represents a phenyl group optionally substituted with a halogen atom or a lower alkyl, hydroxy, hydroxysulfonyloxy or lower alkoxy group optionally substituted with one or more halogen atoms, such as trifluoromethyl.

The invention also encompasses the process for obtaining compounds of formula (I), wherein a compound of formula (II):

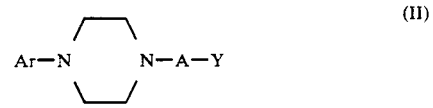

in which A and Ar have the same meaning as in the formula (I) and Y represents a halogen atom, is reacted after dissolution in an organic solvent with a compound of formula (III):

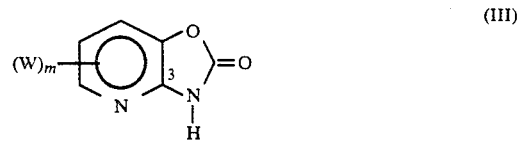

in which W and m have the same meaning as in the formula (I), or its alkali metal addition compound at the 3-position, preferably obtained by dissolution of the compound of formula (III) in an alcoholic solution of an alkali metal ethylate, to lead after heating, preferably under reflux of the reaction medium, cooling, filtration, evaporation of the reaction medium, taking up with water, extraction with an organic solvent preferably selected from chloroform, methylene chloride or ethyl ether and purification by chromatography on a silica column, to a compound of formula (I/A), a special case of the compound of formula (I):

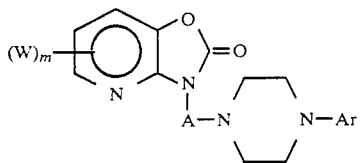

in which W, m and A have the same meaning as above and $R_1$ and $R_2$, with the nitrogen and oxygen which bear them, form an —O—CO—N— linkage, which can, if necessary, be separated into its isomers and, if so desired, salified with a pharmaceutically acceptable acid, which compound of formula (I/A) can be treated, if so desired, with an alkaline agent in aqueous solution, at a temperature between room temperature and the boiling point of the reaction medium, to lead to a derivative of formula (I/B):

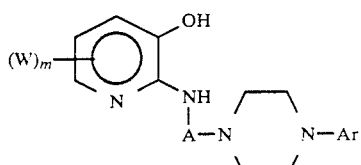

a special case of the compounds of formula (I) for which $R_1$ and $R_2$ each represent a hydrogen atom, which is purified, if necessary, by a technique selected from crystallization or chromatography, and which is salified, if so desired, with a pharmaceutically acceptable acid or base.

The compounds of formula (I/A) may also be obtained by reacting a compound of formula (III):

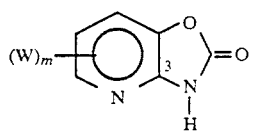

in which W and m have the same meaning as above, with an alkali metal hydroxide in an aqueous medium or an alkali metal alcoholate in an organic medium, to lead to a compound of formula (IV):

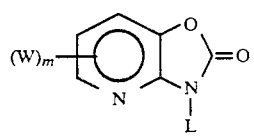

in which W and m have the same meaning as above and L represents an alkali metal, which is condensed with a compound of formula (V):

$$X—A—X'  \qquad (V)$$

in which A has the same meaning as above, and X and X', which may be identical or different, represent a halogen atom, preferably under an inert atmosphere, in an organic medium, preferably at the refluxing temperature of the solvent selected, to lead, after optional extraction and purification by chromatography, to a compound of formula (VI):

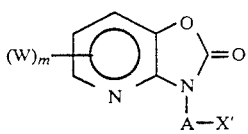

in which W, X', m and A have the same meaning as above, which is condensed, preferably under an inert atmosphere, with a compound of formula (VII), preferably in excess:

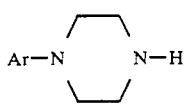

in which Ar has the same definition as above, in an organic medium, in the presence of an excess of a tertiary amine and at the refluxing temperature of the solvent selected, to lead, after cooling, extraction and optional purification by crystallization, to a compound of formula (I) for which A represents a lower alkylene linkage, which can, if necessary, be separated into its isomers and, if so desired, salified with a pharmaceutically acceptable acid.

The latter process may advantageously employ, when A is a linear alkylene linkage, a compound of formula (VIII):

$$X—A—X  \qquad (VIII)$$

a special case of the compounds of formula (V) for which X and X' are identical.

A special case of the compounds of the present invention consists of the compounds of formula (I/A) for which A represents a $CH_2$ group.

The compounds for which A represents a $CH_2$ group and $R_1$ and $R_2$, with the nitrogen and oxygen which bear them, form an O—CO—N linkage will be advantageously obtained in a single step by dissolving, in a lower aliphatic alcohol medium, a derivative of formula (III) as defined above, an arylpiperzine of formula (VII) as defined above, in a slight excess, and an excess of formaldehyde, and heating the solution thereby obtained to a temperature between room temperature and the boiling point of the solution, to lead, after optional cooling, leaving the solution to stand for one to two hours and filtration, and optional chromatography on a silica column, to a compound of formula (I/A1):

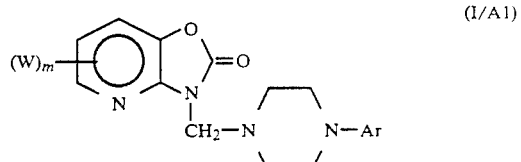

a special case of the compounds of formula (I/A) for which A represents a $CH_2$ linkage, in which W, m and Ar have the same meaning as above, which may be salified, if so desired, with a pharmaceutically acceptable acid.

The compounds of formula (I) possess advantageous pharmacological properties.

In particular, these compounds have evinced an advantageous analgesic activity.

A pharmacological study of the compounds of the invention showed that they were of low toxicity, endowed with a high-level pure analgesic activity, devoid of an anti-inflammatory component and hence devoid of drawbacks inherent in most compounds exhibiting this activity (ulcerogenic action on the mucosae, interference with coagulation, etc.). This spectrum of activity hence renders the compounds for the present invention especially advantageous in a number of indications such as rheumatic pain, such as neuralgia, arteritis, lumbosciatica, pain associated with trauma such as sprains, fractures, dislocations, post-traumatic pain, postoperative pain, dental pain, neurological pain such as facial neuralgia, visceral pain such as nephritic colic, dysmenorrhea, proctological surgery, pancreatitis, various pains, headache, migraine, cancer pain, etc.

The subject of the present invention is also pharmaceutical compositions containing the products of formula (I) or one of their addition salts with the pharmaceutically acceptable acid, alone or in combination with one or more pharmaceutically acceptable, non-toxic, inert vehicles or excipients.

Among the pharmaceutical compositions according to the invention, there may be mentioned, more especially, those which are suitable for oral, parenteral, nasal, rectal, perlingual, ocular or respiratory administration, and in particular injectable preparations, aerosols, eye or nose drops, simple or sugar-coated tablets, sublingual tablets, sachets, packets, hard gelatin capsules, sublingual prepations, pills, suppositories, creams, ointments, skin gels, and the like.

The appropriate dosage varies according to the patient's age and weight, the administration route and the nature of the therapeutic indication and of any associated treatments, and ranges between 1 milligram and 1 gram per 24 hours.

The examples which follow illustrate the invention and in no way limit the latter.

The $^1$H nuclear magnetic resonance spectra were recorded using TMS as an internal reference. The infrared spectra were recorded using a KBr disk containing approximately 1% of the test product.

The products obtained according to the procedures described under the heading "Preparations" do not form part of the invention; they nevertheless constitute synthesis intermediates useful for the preparation of the compound of the invention.

PREPARATIONS

Preparation 1:
4-ARYL-1-(2-CHLOROETHYL)-PIPERAZINES 0.04 mmol of arylpiperazine is dissolved in 40 ml of dimethylformamide. 6.63 g (0.048 mol) of dry potassium carbonate and then 6.88 g (0.048 mol) of 1-bromo-2-chloroethane are added under argon. The mixture is stirred under argon at room temperature for 22 hours. It is filtered to remove the insoluble inorganic matter. The filtrate is acidified with ethanol saturated with dry hydrochloric acid until a pH in the region of 1 is obtained.

400 ml of anhydrous ethyl ether are added. A precipitate of 1-(2-chloroethyl)-4-arylpiperazine hydrochloride appears. The mixture is evaporated and the precipitate obtained is placed in 10% $Na_2CO_3$ solution. The product is extracted with dichlormethane. The organic phase is dried over magnesium sulfate. The organic phase is filtered and evaporated to dryness on a water-bath under vacuum. The product thereby obtained is usable directly in the subsequent reactions.

Preparation 2:
4-ARYL-1-(3-CHLOROPROPYL)-PIPERAZINES

By replacing 1-bromo-2-chloroethane in Preparation 1 by 1-bromo-3-chloropropane, the expected products are obtained.

Preparation 3:
4-ARYL-1-(1-METHYL-1-CHLOROETHYL)PIPERAZINES

By replacing 1-bromo-2-chloroethane in Preparation 1 by 1-bromo-2-chloropropane, the expected products are obtained.

Preparation 4:
3H-OXAZOLO[4,5-b]PYRIDIN-2-ONE*

5.5 g (0.05 mol) of 2-amino-3-hydroxypyridine are introduced into a three-necked flask and the system is placed under argon. 100 ml of anhydrous tetrahydrofuran (THF) are added. 12.15 g (0.075 mol) of 1,1'-carbonyl-diimidazole are then introduced. The mixture is heated to reflux for 5 hours (under argon). The THF is then evaporated off. The residue is taken up with dichloromethane. Washings of the organic phase are performed with NaOH (5%) solution (6×150 ml); the cyclized product passes into the aqueous phase and precipitates at a pH in the region of 5 (by adding 2 N hydrochloric acid solution). The product is filtered off and stored in a desiccator.

*See appended nomenclature

Yield: 77%

Melting point: 212°–214° C.

Preparation 5:
5-METHYL-3H-OXAZOLO[4,5-b]-PYRIDIN-2-ONE

Stage A:
2-NITRO-3-HYDROXY-6-METHYLPYRIDINE 5.45 g (50 mmol) of 5-hydroxy-2-methylpyridine are added to 20 ml of concentrated sulfuric acid, cooling in an ice bath. The temperature is maintained at 30 6° C. and 2.35 ml of fuming nitric acid are added with stirring. The mixture is left overnight at room temperature. 100 g of ice are added with stirring. The product is filtered off, rinsed with water and dried.

Stage B:
2-AMINO-3-HYDROXY-6-METHYLPYRIDINE 3.5 g of 2-nitro-3-hydroxy-6-methylpyridine in 50 ml of methanol are placed under hydrogen pressure in the presence of one gram of palladinized charcoal. The mixture is stirred and filtered. The methanol is evaporated.

Stage C:
5-METHYL-3H-OXAZOLO[4,5-b]PYRIDIN-2-ONE 1.24 g (10 mmol) of 2-amino-3-hydroxy-6-methylpyridine are introduced into a three-necked round-bottomed flask. The system is placed under argon. 20 ml of anhydrous tetrahydrofuran and then 2.43 g (15 mmol) of 1,1'-carbonyldimidazole are added. The mixture is heated to reflux for 6 hours. The reaction medium is evaporated. The crystals obtained are washed with water, filtered off and redissolved in hot methanol. The solution is filtered and re-evaporated.

Yield: 75%.

Melting point 243° C. Spectral characteristics: $^1$H NMR; solvent CDCl$_3$: δ ppm; δ: 12.3 1H, complex, NH; δ: 7.5 1H, doublet; H$_7$; J=8 Hz; δ: 6.9 1H, doublet; H$_6$; J=8 Hz; δ: 2.4 3H; singlet; CH$_3$.

Infrared: 1750 cm$^{-1}$, γ(C=O); 1610 cm$^{-1}$, γ(C=C).

Preparation 6:
3-(2-BROMOETHYL)-3H-OXAZOLO[4,5-b]PYRIDIN-2-ONE

Stage A: OXAZOLO[4,5-b]PYRIDIN-2-ONE SODIUM DERIVATIVE 6 g (44.11 mmol) of 3H-oxazolo[4,5-b]pyridin-2-one are dissolved in a sufficient quantity of tetrahydrofuran, and this solution is then added to an ethanolic solution of sodium ethylate obtained from one gram (44.11 mmol) of sodium in approximately 150 ml of ethanol. The mixture is evaporated under vacuum and the residue is taken up with a sufficient quantity of dimethylformamide to dissolve it.

Stage B:
3-(2-BROMOETHYL)-3H-OXAZOLO[4,5-b]PYRIDIN-2-ONE 7.6 ml (88.22 mmol) of 1,2-dibromoethane, dissolved in approximately 50 ml of dimethylformamide, are placed in a round-bottomed flask under argon surmounted by a condenser, and the solution obtained in the preceding step is then added slowly with stirring. The mixture is brought to 100° C. for 2 hours.

After cooling, the dimethylformamide is evaporated off under vacuum and the residue is then taken up with water and extracted with methylene chloride. After drying over MgSO$_4$, the methylene chloride is evaporated off and the residue is purified on a flash evaporation, 5.2 g of a white powder are obtained.

Yield: 50%..
Melting point: 84° C.

Spectral characteristics: $^1$H NMR—CDCl$_3$—δ: ppm δ: 3.78 2H; triplet; CH$_2$—CH$_2$ Br; J=6.3 Hz; δ: 4.36 2H; triplet; CH$_2$—CH$_2$ Br; J=6.3 Hz; δ: 7.10 1H; doublet of doublet; H$_6$; JH$_6$H$_7$=8.2 Hz; and JH$_6$H$_7$=5.6 Hz. δ: 7.43 1H; doublet of doublet; H$_7$; JH$_7$H$_6$=8.2 Hz; and JH$_7$H$_5$=0.5 Hz. δ: 8.13 1H; doublet of doublet; H$_5$; JH$_5$H$_6$=5.6 Hz; and JH$_5$H$_7$=0.5 Hz.

Infrared: 1760 cm$^{-1}$: γCO.

Employing the same procedure, but using 1,2-dichloroethane, 3-(2-chloroethyl)-3H-oxazolo[4,5-b]-pyridin-2-one is obtained.

Employing the same procedure, but replacing 1,2-dibromoethane by derivatives of general formula:

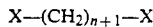

3-(haloalkyl)-3H-oxazolo[4,5-b]pyridin-2-ones are more generally obtained:

Preparation 7:
6-BROMO-3H-OXAZOLO[4,5-b]-PYRIDIN-2-ONE 0.01 mol of oxazolo[4,5-b]pyridin-2-one is dissolved in 100 ml of dimethylformamide. 0.011 mol of bromine is added via a dropping funnel. Stirring is maintained for 1 hour 30 minutes at room temperature and an ice/water mixture is added. The product is filtered off. It is washed with water. The product is dried.

Yield: 90%.
Melting point: 234° C.

Example 1:
3-(4-PHENYL-1-PIPERAZINYLMETHYL)-3H-OXAZOLO[4,5-b]PYRIDIN-2-ONE 4.1 g (0.03 mol) of 3H-oxazolo[4,5-b]pyridin-2-one are dissolved in 100 ml of alcohol at 95° C.

5.35 g (0.033 mol) of 1-phenylpiperzine and then 3 ml of 30% aqueous formaldehyde solution are added. The mixture is stirred on a waterbath at a temperature in the region of 50° C. for 1 h 30 min, stirring being maintained. The mixture is left to stand for 1 hour at room temperature.

The crystals are drained and filtered on a silica column (60Å; 60–220 microns), eluting with dichloromethane.

Yield: 81%.
Melting point: 151°–152° C.

The physicochemical characteristics of this product are seen in Table 1.

Example 2:
3-[4-(3-TRIFLUOROMETHYLPHENYL)-1-PIPERAZINYLMETHYL)-3H-OXAZOLO[4,5-b]-PYRIDIN-2-ONE By replacing 1-phenylpiperazine in Example 1 by 1-(3-trifluoromethylphenyl)piperazine, the expected product is obtained.

Yield: 71%.
Melting point: 112°–118° C.

The physicochemical characteristics of this product are seen in Table 1.

Examples 3 to 8:
3-(4-ARYL-1-PIPERAZINYLMETHYL)-3H-OXAZOLO[4,5-b]PYRIDIN-2-ONES Employing the procedure described in Example 1, but replacing 1-phenylpiperazine by:

Example 3

- 1-(2-chlorophenyl)piperazine, the following is obtained:
3-[4-(2-CHLOROPHENYL)-1-PIPERAZINYLMETHYL]-3H-OXAZOLO[4,5-b]PYRIDIN-2-ONE

Example 4

- 1-(4-fluorophenyl)piperazine, the following is obtained:
3-[4-(4-FLUOROPHENYL)-1-PIPERAZINYLMETHYL]-3H-OXAZOLO[4,5-b]PYRIDIN-2-ONE

Example 5

- 1-(2-methoxyphenyl)piperazine, the following is obtained:
3-[4-(2-METHOXYPHENYL)-1-PIPERAZINYLMETHYL]-3H-OXAZOLO[4,5-b]PYRIDIN-2-ONE

Example 6

- 1-(2-methylphenyl)piperazine, the following is obtained:
3-[4-(2-METHYLPHENYL)-1-PIPERAZINYLMETHYL]-3H-OXAZOLO[4,5-b]PYRIDIN-2-ONE

Example 7

- 1-(3-trifluoromethyl-4-chlorophenyl)piperazine, the following is obtained:

3-[4-(3-TRIFLUOROMETHYL-4-CHLORO-PHENYL)-1-PIPERAZINYLMETHYL]-3H-OXAZOLO[4,5-b]PYRIDIN-2-ONE

Example 8

- 1-(2-pyrimidinyl)piperazine, the following is obtained:
3-[4-(2-PYRIMIDINYL)-1-PIPERAZINYLME-THYL]-3H-OXAZOLO[4,5-b]PYRIDIN-2-ONE

Example 9

- 1-(1-naphthyl)piperazine, the following is obtained:
3-[4-(1-NAPHTHYL)-1-PIPERAZINYLMETHYL]-3H-OXAZOLO[4,5-b]PYRIDIN-2-ONE

Example 10

- 1-(2-pyridyl)piperazine, the following is obtained:
3-[4-(2-PYRIDYL)-1-PIPERAZINYLMETHYL]-3H-OXAZOLO[4,5-b]PYRIDIN-2-ONE

Example 11

- 1-(1-isoquinolyl)piperazine, the following is obtained:
3-[4-(1-ISOQUINOLYL)-1-PIPERAZINYLME-THYL]-3H-OXAZOLO[4,5-b]PYRIDIN-2-ONE

Example 12

- 1-(2-quinolyl)piperazine, the following is obtained:
3-[4-(2-QUINOLYL)-1-PIPERAZINYLMETHYL]-3H-OXAZOLO[4,5-b]PYRIDIN-2-ONE

Example 13

- 1-(2-thiazolyl)piperazine, the following is obtained:
3-[4-(2-THIAZOLYL)-1-PIPERAZINYLMETHYL]-3H-OXAZOLO[4,5-b]PYRIDIN-2-ONE

Example 14

3-[2-(4-PHENYL-1-PIPERAZINYL)-ETHYL]-3H-OXAZOLO[4,5-b]PYRIDIN-2-ONE

WORKING METHOD 1

1.13 g (0.049 mol) of sodium are dissolved in 600 ml of ethanol. 6.6 g (0.049 mol) of 3H-oxazolo-[4,5-b]pyridin-2-one are added to the solution obtained above. The mixture is stirred vigorously at room temperature and the ethanol is then evaporated off.

11.0 g (0.049 mol) of 4-phenyl-1-(2-chloroethyl)-piperazine, obtained according to the protocol of Preparation 1, is dissolved separately in 50 ml of dimethylformamide, and the 3H-oxazolo[4,5-b]pyridin-2-one sodium derivative prepared above is added slowly and with stirring. The mixture is heated to reflux for 1 h 30 min. After cooling, the insoluble inorganic matter is drained and the filtrate is evaporated on a waterbath under vacuum.

The residue is taken up with water and purified by extraction with dichlormethane. The residue obtained is filtered on a silica column, eluting directly with dichlormethane.

Yield: 59%.

WORKING METHOD 2

In a round-bottomed flask placed under argon and surmounted by a condenser, 1.5 equivalents of 1-phenylpiperazine and then 1.5 equivalents of diisopropylethyl)-3H-oxazolo[4,5-b]pyridin-2-one obtained in Preparation 6. The mixture is brought to 80° C. for 12 hours. After cooling, the acetonitrile is evaporated off under vacuum and the residue is taken up with water. The alkalinity of the medium is checked and the product is extracted with dichloromethane. The organic phase is dried over magnesium sulfate and evaporated and the product is recrystallized.

Yield: 95%.
Melting point: 105°–110° C.

The physicochemical characteristics of this compound are seen in Table 1.

Example 15

3-{2-[4-(3-TRIFLUOROMETHYLPHENYL)-1-PIPERAZINYL]ETHYL}-3H-OXAZOLO[4,5-b]PYRIDIN-2-ONE

Employing the procedure described in Example 14, working method 1, but replacing 4-phenyl-1-(2-chloroethyl)piperazine by 4-(3-trifluoromethylphenyl)-1-(2-chloroethyl)piperazine, the expected product is obtained.

Yield: 40%.
Melting point: 92°–93° C.

The physicochemical characteristics of this compound appear in Table 1.

Example 16

3-[3-(4-PHENYL-1-PIPERZINYL)-PROPYL]-3H-oxazolo[4,5-b]-pyridin-2-one

Employing the procedure described in Example 14, working method 1, but replacing 4-phenyl-1-(2-chloroethyl)piperazine by 4-phenyl-1-(3-chlorophenyl)-piperazine, the expected product is obtained.

Yield: 47%.
Melting point: 141°–142° C.

The physicochemical characteristics of this compound appear in Table 1.

Example 17

3-{3-[4-(3-TRIFLUOROMETHYLPHENYL)-1-PIPERAZINYL]PROPYL}-3H-OXAZOLO[4,5-b]PYRIDIN-2-ONE

Employing the procedure described in Example 14, working method 1, but replacing 4-phenyl-1-(2-chloroethyl)piperazine by 4-(3-trifluoromethylphenyl)-1-(3-chloropropyl)piperzine, the expected product is obtained.

Yield: 63%.
Melting point: 62°–63° C.—see Table 1.

Examples 18 to 21

By replacing 4-phenyl-1-(2-chloroethyl)piperazine in Example 14, working method 1, by:

Example 18

- 4-(2methoxyphenyl)-1-(2-chloroethyl)piperazine, the following is obtained:
3-{2-[4-(2-METHOXYPHENYL)-1-PIPERAZINYL]ETHYL{-3H-OXAZOLO[4,5-b]PYRIDIN-2-ONE
Yield: 53%
Melting point: 95°–96° C. (see Table 1).

Example 19

- 4-(2-chlorophenyl)-1-(2-chloroethyl)piperazine, the following is obtained:
3-{2-[4-(2-CHLOROPHENYL)-1-PIPERAZINYLE-THYL}-3H-OXAZOLO[4,5-b]PYRIDIN-2-ONE

Example 20

- 4-(2-methylphenyl)-1-(2-chloroethyl)piperazine, the following is obtained:

3-{2-[4-(2-METHYLPHENYL)-1-PIPERAZINYL]E-
THYL}-3H-OXAZOLO[4,5-b]PYRIDIN-2-ONE

Example 21

4-(3-trifluoromethyl-4chlorophenyl)-1-(2-chloroe-thyl)piperazine, the following is obtained:
3-{2-[4-(3-TRIFLUOROMETHYL-4-CHLORO-
PHENYL)-1-PIPERAZINYL]ETHYL}-3H-
OXAZOLO[4,5-b]PYRIDIN-2-ONE Examples 22 to 25

By replacing 1-phenylpiperazine in Example 14, working method 2, by:

Example 22

- 1-(2-pyrimidinyl)piperazine, the following is obtained:
3-{2-[4-(2-PYRIMIDINYL)-1-PIPERAZINYL]E-
THYL}-3H-OXAZOLO[4,5-b]PYRIDIN-2-ONE
Melting point: 150° C.

Example 23

1-(4-fluorophenyl)piperazine, the following is obtained:
3-{2-[4-(4-FLUOROPHENYL)-1-PIPERAZINYL]E-
THYL}-3H-OXAZOLO[4,5-b]PYRIDIN-2-ONE
Yield: 95%
Melting point: 94° C.—see Table 1

Example 24

- 1-(4-phenoxyphenyl)piperazine, the following is obtained:
3-{2-[4-(4-PHENOXYPHENYL)-1-PIPERAZINYL-
]ETHYL}-3H-OXAZOLO[4,5-b]PYRIDIN-2-ONE
Yield: 92%.
Melting point: 148° C.
Spectral characteristics: Infrared: 1760$\gamma$ CO
$^1$H NMR (CHCl$_3$): $\delta = 6.8$–6.9 and 7.2–7.3, 9H complex, aromatic protons.

Example 25

- 1-(4-chlorophenyl)piperazine, the following is obtained:
3-{2-[4-(4-CHLOROPHENYL)-1-PIPERAZINYL]E-
THYL}-3H-OXAZOLO[4,5-b]PYRIDIN-2-ONE
Melting point: 110° C.
Spectral characteristics: Infrared: 1760$\gamma$ OCON Example 26

- 1-(2-pyridyl)piperazine, the following is obtained:
3-{2-[4-(2-PYRIDYL)-1-PIPERAZINYL]ETHYL}-
3H-OXAZOLO[4,5-b]PYRIDIN-2-ONE
Melting point: 148° C.
Spectral characteristics: Infrared: 1760$\gamma$ CO.

Examples 27 to 32

By replacing the 4-aryl-1-(2-chloroethyl)-piperazines in Examples 18 to 22 by the corresponding 4-aryl-1-(3-chloropropyl)piperazines, the following are obtained:
3-[3-(4-ARYL-1-PIPERAZINYL)PROPYL]-3H-
OXAZOLO-[4,5-b]PYRIDIN-2-ONES Example 33

3-{2-(4-PHENYL-1-PIPERAZINYL)-ETHYL]-5-
METHYL-3H-OXAZOLO[4,5-b]PYRIDIN-2-ONE

By replacing 3H-oxazolo[4,5-b]pyridin-2-one in Example 14 by 5-methyl-3H-oxazolo[4,5-b]pyridin-2-one obtained in Preparation 5, the product of the title is obtained.
Yield: 50%
Melting point: 100°–102° C.

Example 34

3-{2-(4-PHENYL-1-PIPERAZINYL)-ETHYL]-6-
BROMO-3H-OXAZOLO[4,5-b]PYRIDIN-2-ONE

By replacing 3H-oxazolo[4,5-b]pyridin-2-one in Example 14 by 6-bromo-3H-oxazolo[4,5-b]pyridin-2-one obtained in Preparation 7, the product of the title is obtained.
Melting point: 110° C.

Example 35

3-{2-[4-(4-METHOXYPHENYL-1-
PIPERAZINYL]ETHYL}-3H-OXAZOLO[4,5-
b]PYRIDIN-2-ONE

By replacing 4-phenyl-1-(2-chloroethyl)piperazine in Example 14 working method 1, by 4-(4-methoxyphenyl)-1-(2chloroethyl)piperazine, 3-{2-[4-(4methoxyphenyl)-1piperazinyl]ethyl}-3H-oxazolo[4,5-b]pyridin-2-one is obtained.
Yield: 48%.
Melting point: 125° C.

Example 36

3-{2-[4-(4-HYDROXYPHENYL)-1-PIPERAZINYL-
]ETHYL}-3H-OXAZOLO[4,5-b]PYRIDIN-2-ONE 140 ml (140 mmol) of a 1 M solution of boron tribromide in dichloromethane are added under a stream of nitrogen and at a temperature of $-70°$ C. to a solution of 5 grams (14.1 mmol) of 3-{2-[4-(4-methoxyphenyl)-1-piperazinyl]ethyl}-3H-oxazolo[4,5-b]pyridin-2-one in 250 ml of dichloromethane. After the addition, stirring reaction medium is neutralized with a molar solution of sodium hydrogen carbonate and extracted with methylene chloride.

The organic phase is dried, and evaporated under reduced pressure. The residue is chromatographed on a silica column (eluant: cyclohexane/ethyl acetate, 6:4).
Yield: 30%
Melting point: 159° C.

Using the procedures described in Examples 14, working method 1, and 15 to 21, but replacing the 4-aryl-1-(2-chloroethyl)piperazines and 4-aryl-1-(3-chloropropyl)piperazines by:
- 4-aryl-1-(4-chloro-n-butyl)piperazines, 3-[4-(4-aryl-1-piperazinyl)butyl]-3H-oxazolo-[4,5-b]pyridin-2-ones are obtained;
- 4-aryl-1-(5-chloro-n-pentyl)piperazines, 3-[5-(4-aryl-1-piperazinyl)pentyl]-3H-oxazolo-[4,5-b]pyridin-2-ones are obtained;
- 4-aryl-1-(6-chloro-n-hexyl)piperazines, 3-[6-(4-aryl-1-piperazinyl)hexyl]-3H-oxazolo-[4,5-b]pyridin-2-ones are obtained;
- 4-aryl-1-(1-methyl-1-chloroethyl)piperazines, 3-[2-(4-aryl-1-piperazinyl)-1-methylethyl]-3H-oxazolo-[4,5-b]pyridin-2-ones are obtained.

Employing the procedures described in Examples 14, working method 2, and 22 to 25, but replacing 3-(2-bromoethyl)-3H-oxazolo[4,5-b]pyridin-2-one by:
- 3-(3-bromopropyl)-3H-oxazolo[4,5-b]pyridin-2-one, 3-[3-(4-aryl-1-piperazinyl)propyl]-3H-oxazolo[4,5-b]pyridin-2-ones are obtained;
- 3-(4-bromo-n-butyl)-3H-oxazolo[4,5-b]pyridin-2-one, 3-[4-(4-aryl-1-piperazinyl)-n-butyl]-3H-oxazolo[4,5-b]pyridin-2-ones are obtained;

- 3-(5-bromo-n-pentyl)-3H-oxazolo[4,5-b]pyridin-2-one, 3-[5-(4-aryl-1-piperazinyl)-n-pentyl]-3H-oxazolo[4,5-b]pyridin-2-ones are obtained;
- 3-(6-bromo-n-hexyl)-3H-oxazolo[4,5-b]pyridin-2-one, 3-[6-(4-aryl-1-piperazinyl)-n-hexyl]-3H-oxazolo[4,5-b]pyridin-2-ones are obtained.

The syntheses of the above examples are also applicable to 3H-oxazolo[4,5-b]pyridin-2-one derivatives substituted on the aromatic ring with one or more halogen atoms or a lower alkyl or alkoxy group optionally substituted with one or more halogen atoms.

Example 1A
2-[2-(4-PHENYL-1-PIPERAZINYL)-ETHYLAMINO]-3-PYRIDINOL 0.01 mol of 3-[2-(4-phenyl-1-piperazinyl)ethyl]-3H-oxazolo[4,5-b]pyridin-2-one, obtained in Example 14, is placed in 50 ml of 10% sodium hydroxide solution. The mixture is heated to reflux for four hours with magnetic stirring. After cooling, the solution is acidified with 30% hydrochloric acid. Saturated aqueous sodium bicarbonate solution is added to pH 7 while the mixture is cooled. The precipitate is filtered off and washed three times with water, dried under vacuum in a desciccator and then washed again with dichloromethane.

Melting point: 191° C.

Employing the procedure described in Example 1A, but using as a starting material the compounds obtained in Examples 1 to 36, the following are obtained:
- 2-{[4-(substituted or unsubstituted aryl)-piperazinyl]alkylamino}-3-pyridinols, optionally substituted.

PHARMACOLOGICAL STUDY OF THE COMPOUNDS OF THE INVENTION

Example A: Study of the acute toxicity

The acute toxicity was assessed after oral administration to batches 8 mice (26±2 grams). The animals were observed at regular intervals during the first day, and daily during the 2 weeks following the treatment. The $LD_{50}$, the dose causing the death of 50% of the animals, was evaluated.

The $LD_{50}$ of the products according to the invention which were tested is greater than 1000 mg/kg with the exception of that of Examples 1 and 2 for which it is in the region of 500 mg/kg, which indicates the low toxicity of the compounds of the invention.

Example B: Study of the analgesic activity

The activity against pain was investigated in mice (23-25 g) according to a protocol derived from the technique described by SIEGMUND (SIEGMUND E.A., R.A. CADMUS & GOLU, J. Pharm. Exp. Ther. 119, 184, 1957). The mice, randomized in batches of 12 animals, received the treatment orally (excipient for the controls) 1 hour before the intraperitoneal injection of a 0.02% aqueous-alcoholic solution of phenyl-p-benzoquinone. The writhing movements are counted between the 5th and 10th minute after injection.

The percentage activity obtained was evaluated for each dose (% decrease in the number of writhing movements in the treated animals relative to the controls). An $ED_{50}$, the dose producing a 50% activity, was determined for each product tested.

It was apparent that the compounds of the invention possess a very advantageous analgesic activity.

Thus, the $ED_{50}$ of the compound of Examples 14 and 15 is in the region of the one mg.kg$^{-1}$.

By way of comparison, the $ED_{50}$ of the product of Example 6 (2-(2-fluorophenyl)oxazolo[4,5-b]pyridine) of U.S. Pat. No. 4,038,396 in the same test is in the region of 12 mg.kg$^{-1}$.

Example C: Study of the anti-inflammatory activity

The anti-inflammatory potential of the compounds was investigated on a model of acute inflammation induced by the subcontaneous injection of a solution of carrageenan into the rat hind foot, according to a technique based on the method of WINTER, C.A., E.A. RISLEY and G.N. NUSS (Proc. Soc. Exp. Med. 111, 554, 1962). The rats (100-120 g), randomized in batches of 8, were treated (including the controls, which receive excipient) 1 hour before the local injection of a 0.5% suspension of carrageenan (Sigma type IV; 0.1 ml per rat). The edema is determined 3 hours after injection, by plethysmometric measurement (UGO BASILE water plethsometer) of the volume of each of the hind feet (edema=volume of the inflamed foot—volume of the non-inflamed foot).

The percentage activity corresponds to the percentage decrease in the mean edema of the batch compared with the mean of the corresponding control batch. An $ED_{30}$, the dose producing a 30% activity, was determined.

This $ED_{30}$ is equal to 50 mg.kg$^{-1}$ for the compound of Example 6 of U.S. Pat. No. 4,038,396. It is very markedly greater than this value for all the compounds of the invention.

The pharmacological study of the products of the invention hence shows that these products are of low toxicity, endowed with an analgesic activity more intense than that of the compounds of related structure of the prior art, and devoid of anti-inflammatory activity in contrast to these same compounds of the prior art.

Example D: Pharmaceutical composition: TABLET

Tablets containing 25 mg of 3-[2-(4-phenyl-1-piperazinyl)ethyl]-3H-oxaxolo[4,5-b]pyridin-2-one.

Preparation formula for 1000 tablets

| Preparation formula for 1000 tablets. | |
| --- | --- |
| 3-[2-(4-Phenyl-1-piperazinyl)ethyl]-3H-oxazolo[4,5-b]pyridin-2-one | 25 g |
| Wheat starch | 15 g |
| Corn starch | 15 g |
| Lactose | 65 g |
| Magnesium stearate | 2 g |
| Silica | 1 g |
| Hydroxypropylcellulose | 2 g |

TABLE 1

| SPECTRAL CHARACTERISTICS OF SOME COMPOUNDS OF THE INVENTION (formulae: see Appendix) | | | | | |
| --- | --- | --- | --- | --- | --- |
| EX | p* | R | Infrared | Nuclear Magnetic Resonance (δ:ppm) | |
| 1 | 1 | H | 3100-2785:ν CH<br>1750:ν CO<br>1590:ν C=C | δ:2.91-2.96; 4H; comp; A—A'δ:3.18-3.22; 4H; comp; B—B'<br>δ:5.00; 2H; s; N—CH$_2$—N; δ:6.80-6.92 ppm; 3H; comp; Ha, a', c<br>δ:7.03; 1H; dd, H$_6$. JH$_6$H$_7$=8.3 Hz and JH$_6$H$_5$=5.4 Hz | |

TABLE 1-continued

SPECTRAL CHARACTERISTICS OF SOME COMPOUNDS OF THE INVENTION
(formulae: see Appendix)

| EX | p | R | T | Infrared | Nuclear Magnetic Resonance ($\delta$: ppm) |
|---|---|---|---|---|---|
| | | | | conjugated | $\delta$:7.2–7.3 (2H, comp):Hb, b' |
| | | | | | $\delta$:7.37; 1H; dd; H7; JH6H7 = 8.3 Hz and JH5H7 = 1 Hz |
| | | | | | $\delta$:8.10; 1H; dd; H5; JH5H6 = 5.4 Hz and JH5H7 = 1 Hz |
| 2 | 1 | mCF3 | | 3100-2785:$\nu$ CH | $\delta$:2.85–3.05; 4H; comp; AA'$\delta$:3.15-3.35 ppm; 4H; BB' |
| | | | | 1750:$\nu$ CO | $\delta$:5.00; 2H; s; N—CH2—N$\delta$:6.9-7.15 ppm; 4H; comp; Ha, a', c and H6 |
| | | | | 1590:$\nu$ C=C | $\delta$:7.20-7.45; 2H; comp; H7 and Hb |
| | | | | conjugated | $\delta$: 8.10; 1H; dd; H5; JH5H6 = 4.8 Hz and JH5H7 = 1 Hz |
| 14 | 2 | H | | 3000-2700:$\nu$ CH | $\delta$:2.66-2.72; 4H; comp; AA' $\delta$: 2.85; 2H; t; CH2—$\underline{CH_2}$-pipe; J=6.6 Hz |
| | | | | 1750;$\nu$ CO | $\delta$:3.07-3.13; 4H; comp; BB'$\delta$:4.10; 2H; t; $\underline{CH_2}$—CH2-pipe; J=6.6 Hz |
| | | | | 1590: $\nu$ C=C | $\delta$:6.79—6.91; 3H; comp; Ha, a'; c $\delta$:7.19—7.27; 2H; comp; Hb, b' |
| | | | | conjugated | $\delta$:7.03; 1H; dd; H6; JH6H7 = 8 Hz and JH5H6 = 4 Hz |
| | | | | | $\delta$:7.38;1H; dd; H7; JH5H7 = 0.3 Hz and JH6H7 = 8 Hz |
| | | | | | $\delta$:8.10; 1H; dd; H5; JH5H6:5.4 Hz and JH5H7 = 0.3 Hz |
| 15 | 2 | mCF3 | | 3000-2700:$\nu$ CH | 2.65-2.75 ppm; 4H; comp; AA'2.85; 2H; t; CH2—$\underline{CH_2}$-pipe; J=6.6 Hz |
| | | | | 1750:$\nu$ CO | 3.0-3.2 ppm; 4H; comp; BB'4.10; 2H; t; $\underline{CH_2}$—CH2; pipe; J=6.6 Hz |
| | | | | 1590:$\nu$ C=C | 6.90-7.15; 4H; comp; H6 and Ha, a', c 7.25-7.45; 2H; comp; H7 and Hb |
| | | | | conjugated | 8.10; 1H; dd; H5; JH5H7 = 0.3 Hz and JH5H6 = 4.8 Hz |
| 16 | 3 | H | | 3000-2700:$\nu$ CH | 2.0-2.1; 2H; comp; CH2—CH2—$\underline{CH_2}$-pipe 2.46-2.56; 6H; comp; CH2$\underline{CH_2}$CH2 pipe, AA' |
| | | | | 1750:$\nu$ CO | 3.0–3.1; 4H: comp; BB' 4.07; 2H; t; $\underline{CH_2}$—CH2—CH2-pipe; J=6.6 Hz |
| | | | | 1590:$\nu$ C=C | 7.03; 1H; H6; J=H6H7 = 8 Hz and 7.19-7.28; 2H; comp; Hbb' |
| | | | | conjugated | 7.37; 1H; dd; JH6H7 = 8 Hz and JH5H7 = 0.3 Hz:H7 |
| | | | | | 6.80-6.92; 3H; comp; Haa'c and JH6H7 = 8 Hz |
| | | | | | 8.10; 1H; dd; H5JH5H7 = 0.3 Hz and JH5H6 = 5.4 Hz |
| 17 | 3 | mCF3 | | 3000-2700:$\nu$ CH | 2.0-2.1; 2H; comp; CH2CH2$\underline{CH_2}$ pipe 2.45-2.55; 6H; comp; CH2$\underline{CH_2}$CH2 pipe, AA' |
| | | | | 1750: $\nu$ CO | 3.0–3.1; 4H:comp:BB' 4.07; 2H; t; $\underline{CH_2}$—CH2—CH2-pipe; J=6.6 Hz |
| | | | | 1590: $\nu$ C=C | 6.9-7.15; 4H; comp; H6 and Haa'b 7.25-7.45; 2H; comp; H7 Hb |
| | | | | conjugated | 8.10; 1H; dd; H5; JH5H7 = 0.3 Hz and JH5H6 = 5.4, Hz |
| EX | p | R | T | Infrared | Nuclear Magnetic Resonance ($\delta$: ppm) |
| 18 | 2 | OCH3 | H | 3100-2630:$\nu$ CH | 2.69-2.78; 4H; comp; AA' 2.86; 2H; t; CH2—$\underline{CH_2}$-pipe; J=6.7 Hz |
| | | | | 1780:$\nu$ C=O | 2.92-3.03; 4H; comp; BB' 3.84; 3H; s; —O$\underline{CH_3}$ |
| | | | | 1590:$\nu$ C=C | 4.10; 2H; t; C$\underline{H_2}$—CH2 pipe J=6.7 Hz 6.82–6.90; 2H; comp; $H_a$'Hz |
| | | | | conjugated | 6.92-7.02; 2H; comp; Hb, Hb' 7.03; 1H; dd; H6; JH6—H7 = 7.6 Hz |
| | | | | | 7.38; 1H; dd; H7; JH7—H6 = 7.6 Hz; JH7H5 = Hz |
| | | | | | 8.09; 1H; dd; H5; JH5—H6 = 5.0 Hz; JH5H7; 1 Hz |
| 23 | 2 | pF | H | 3100-2600:$\nu$ CH | 2.69-2.78; 4H; comp; AA' 2.88; 2H; t; CH2$\underline{CH_2}$ pipe; J=6.3 Hz |
| | | | | 1720:$\nu$ CO | 3.01-3.10; 4H; comp:BB' 4.12; 2H; t; $\underline{CH_2}$CH2 pipe; j=6.3 Hz |
| | | | | 1590:$\nu$ C=C | 6.79-6.87; 2H; comp; HaHa' 6.88-6.97; 2H; comp; HbHb' |
| | | | | conjugated | 7.04; 1H; dd; H6; JH6H7 = 7.3 Hz; JH6H5 = 5.3 Hz |
| | | | | | 7.38; 1H; dd; Hz; JH7H6 = 7.7 Hz; JH7H5 = 1 Hz |
| | | | | | 8.10; 1H; dd; H5; JH5H6 = 5.3 Hz and JH5H7 = 1 Hz |
| 31 | 2 | H | 5-CH3 | 3000-2610:$\nu$ CH | 2.51; 3H; s; —CH3 2.66-2.74; 4H; comp; AA' |
| | | | | 1700:$\nu$ CO | 2.82; 2H; t; CH2—$\underline{CH_2}$-pipe; J=6.4 Hz 3.05-3.14; 4H; comp; BB' |
| | | | | 1590:$\nu$ C=C | 4.08; 2H; t; $\underline{CH_2}$—CH2 pipe; J=6.4 Hz 6.80-6.90; 4H; comp; H6 Ha,Ha', H6 |
| | | | | conjugated | 7.2-7.3; 3H; comp; H7, Hb, Hb' | comp: complex; t: triplet; dd: doublet of doublet; pipe: piperazine; p = n +1 when B = H T = H

APPENDIX

TABLE FORMULA

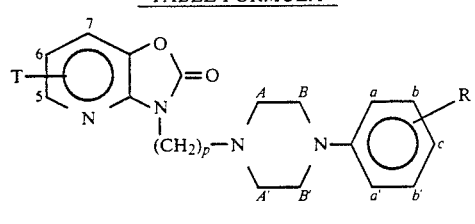

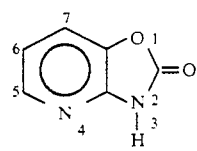

3H-oxazolo[4,5-b]pyridin-2-one

We claim:

1. A compound selected from those of formula (I):

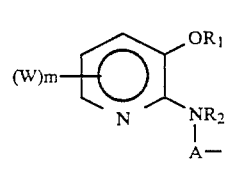

(I)

in which:

R1 and R2 each represent a hydrogen atom or, with the oxygen and nitrogen which bear them, form an —O—CO—N-linkage, W represents a halogen atom or a lower alkyl or lower alkyloxy group optionally substituted with one to three halogen atoms, inclusive, and m being 0 to 3, inclusive, A represents a linear or branched lower alkylene group, and Ar represents phenyl, naphthyl, pyridyl, pyrimidinyl, quinolyl, isoquinolyl, or thiazolyl, optionally substituted with one or two halogen atoms or with one two lower alkyl, hydroxy, hydroxysulfonyloxy, lower alkyloxy, or phenyloxy groups optionally substituted with one to three halogen atoms, inclusive, the term "lower alkyl" in lower alkyl and lower alkyloxy being understood to mean a linear or branched alkyl group having 1 to 6 carbon atoms, inclusive, their isomers, and their addition salts with a pharmaceutically-acceptable acid and, when $R_1$ and $R_2$ represent a hydrogen atom, their addition salts with a pharmaceutically-acceptable base.

2. A compound as claimed in claim 1 in which $R_1$ and $R_2$ together form a CO group, of formula (I/A):

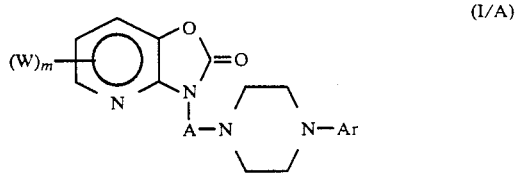

its isomers and its addition salts with a pharmaceutically-acceptable acid.

3. A compound as claimed in claim 1 in which $R_1$ and $R_2$ each represent a hydrogen atom, of formula (I/B):

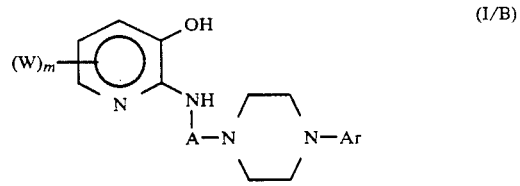

its isomers and its addition salts with a pharmaceutically-acceptable acid or with a pharmaceutically acceptable base.

4. A compound as claimed in claim 1 in which Ar represents a phenyl group optionally substituted with a halogen atom or with a lower alkyl, hydroxy, hydroxysulfonyloxy or lower alkyloxy group, these groups themselves being optionally substituted with one to three, inclusive, halogen atoms, and its addition salts with a pharmaceutically-acceptable acid or, when $R_1$ and $R_2$ represent a hydrogen atom, its isomers and its addition salts with a pharmaceutically-acceptable base.

5. A compound of claim 4 in which Ar represents trifluoromethylphenyl.

6. A compound as claimed in claim 1, which is selected from 3-[4-(3-trifluoromethylphenyl)-1-piperazinyl]-3H-oxazolo[4,5-b]pyridin-2one and its addition salts with a pharmaceutically-acceptable acid.

7. A compound as claimed in claim 1, which is selected from 3-(4-phenyl-1-piperazinylmethyl)-3H-oxazolo[4,5-b]pyridin-2-one and its addition salts with a pharmaceutically-acceptable acid.

8. A compound as claimed in claim 1, which is selected from 3-{2-[4-(3-trifluoromethylphenyl)-1-piperazinyl]ethyl}-3H-oxazolo[4,5-b]pyridin-2one and its addition salts with a pharmaceutically-acceptable acid.

9. A compound as claimed in claim 1, which is selected from 3-{3-[4-(3-trifluoromethylphenyl)-1-piperazinyl]propyl}-3H-oxazolo[4,5-b]pyridin-2one and its addition salts with a pharmaceutically-acceptable acid.

10. A compound as claimed in claim 1, which is selected from 3-{2-[4-(4-phenyl-1-piperazinyl)ethyl]-3H-oxazolo-[4,5-b]pyridin-2-one and its addition salts with a pharmaceutically-acceptable acid.

11. A compound as claimed in claim 1, which is selected from 3-{2-[4-(2-pyridyl)-1-piperazinyl]ethyl}-3H-oxazolo[4,5-b]pyridin-2one and its addition salts with a pharmaceutically-acceptable acid.

12. A compound as claimed in claim 1, which is selected from 3-{2-[4-(2-pyrimidinyl)-1-piperazinyl]ethyl}-3H-oxazolo[4,5-b]pyridin-2one and its addition salts with a pharmaceutically-acceptable acid.

13. A compound as claimed in claim 1, which is selected from 2-[2-(4-phenyl-1-piperazinyl)ethylamino]-3-pyridinol and its addition salts with a pharmaceutically-acceptable acid or base.

14. A pharmaceutical composition containing, as active principle at least one compound as claimed in claim 1, in combination with one or more pharmaceutically acceptable, non-toxic, inert vehicles or excipients.

15. A method for treating a living animal afflicted with pain comprising the step of administering to the said living animal amount of a compound of claim 1 which is suitable for the alleviation of said condition.

* * * * *

UNITED STATES PATENT AND TRADEMARK OFFICE
CERTIFICATE OF CORRECTION

PATENT NO. : 5,084,456

DATED : Jan. 28, 1992

INVENTOR(S) : Gerald Guillaumet, Christine Flouzat, Jacqueline Bonnet

It is certified that error appears in the above-identified patent and that said Letters Patent is hereby corrected as shown below:

Column 1, approximately line 33; "base" should read -- best --.
Column 1, approximately line 41; "avoid" should read -- devoid --.
Column 2, lines 24/25; after "example.", insert the paragraph
   -- Among bases which may be added to the compounds of formula (I) for which $R_1$ and $R_2$ each represent a hydrogen atom, sodium, potassium and calcium hydroxides and carbonates may be mentioned by way of example. --.
Column 2, last line; "compound" should read -- compounds --.
Column 5, line 23; "with the pharma-" should read
   -- with a pharma- --
Column 5, approximately line 51; "compound" should read
   -- compounds --.
Column 6, line 46; "at 30 6°C." should read -- at +6°C. --.
Column 7, line 8; "$cm^{-1}, \gamma(C=O);$" should read --$cm^{-1}, \nu(C=O);$--.
Column 7, line 8; "$cm^{-1}, \gamma(C=C).$ should read --$cm^{-1}, \nu(C=C).$--.
Column 7, line 38; "flash evapora-" should read -- flash silica column (230-240 mesh) in methylene chloride. After evapora- --.
Column 7, line 49; "$cm^{-1}: \gamma CO.$" should read --$cm^{-1}: \nu CO.$--.
Column 9, line 64 ; "propylethyl)-3H" should read -- propylethylamine are added to 2.43 g (0.01 mol) of 3-(2-bromoethyl) -3H --.
Column 10, line 24; "PIPERZINYL" should read -- PIPERAZINYL --.
Column 10, approximately line 29; "(3-chlorophenyl)" should read
   -- (3-chloropropyl) --.
Column 10, approximately line 53; ""-4-(2methoxyphenyl)-"
   should read -- -4-(2-methoxyphenyl)- --.
Column 10, approximately line 56; move the closing bracket "]" from the beginning of line 56 to the end of line 55 and insert after "PIPERAZINYL" and before the hyphen.
Column 10, line 56; "ETHYL {-3H-" should read --ETHYL} - 3H- --.

UNITED STATES PATENT AND TRADEMARK OFFICE
CERTIFICATE OF CORRECTION

PATENT NO. : 5,084,456

DATED : Jan. 28, 1992

INVENTOR(S) : Gérald Guillaumet, Christine Flouzat, Jacqueline Bonnet

It is certified that error appears in the above-identified patent and that said Letters Patent is hereby corrected as shown below:

Column 10, line 63/64; move the "E" from the end of line 63 to the beginning of line 64 and insert before "THYL".
Column 11, line 5; "4-(3-trifluoromethyl-4chlorophenyl) should read -- 4-(3-trifluoromethyl-4-chlorophenyl) --.
Column 11, lines 17/18; move the "E" from the end of line 17 and insert at the beginning of line 18 before "THYL".
Column 11, lines 23/24; move the "E" from the end of line 23 and insert at the beginning of line 24 before "THYL".
Column 11, lines 31/32; move the "]" from the beginning of line 32 and insert at the end of line 31 after "PIPERAZINYL" and before the hyphen.
Column 11, line 35; "1760 γ CO" should read -- 1760 ν CO --.
Column 11, line 42; move the "E" from the end of line 42 and insert at the beginning of line 43 before "THYL".
Column 11, line 45; "1760 γ OCON" should read --1760 ν OCON--.
Column 12, line 4; "3-[2-" should read -- 3-[2- --.
Column 12, line 14; "(4-METHOXYPHENYL-1- " should read -- (4-METHOXYPHENYL)-1- --.
Column 12, line 19; "(2chloroethyl)" should read -- (2-chloroethyl) --.
Column 12, line 19; "(4methoxy-" should read --(4-methoxy- --.
Column 12, line 20; "1piperazinyl" should read --1-piperazinyl--.
Column 12, line 26/27; move the "]" from the beginning of line 27 and insert at the end of line 26 before the hyphen.
Column 12, line 34/35; "stirring reaction" should read -- stirring is maintained for 24 hours at room temperature. The reaction--.
Column 13, lines 30/31; move the "]" from the beginning of line 31 and insert at the end of the line 30 before the hyphen.
Column 14, approximately line 47; "oxaxolo" should read --oxazolo--.

Column 17, lines 9/10; "with one two" should read -- with one or two --.

UNITED STATES PATENT AND TRADEMARK OFFICE
CERTIFICATE OF CORRECTION

PATENT NO.   : 5,084,456

DATED        : Jan. 28, 1992

INVENTOR(S)  : Gérald Guillaumet, Christine Flouzat, Jacqueline Bonnet

It is certified that error appears in the above-identified patent and that said Letters Patent is hereby corrected as shown below:

Column 18, Claims 6, 8, 9, 11, 12; line 3 in each instance; "-2one" should read -- -2-one --.

Signed and Sealed this

Twenty-fifth Day of October, 1994

Attest:

BRUCE LEHMAN

*Attesting Officer*       *Commissioner of Patents and Trademarks*

UNITED STATES PATENT AND TRADEMARK OFFICE
CERTIFICATE OF CORRECTION

PATENT NO. : 5,084,456
DATED : January 28, 1992
INVENTOR(S) : Gerald Guillaumet, Christine Flouzat and Jacqueline Bonnet It is certified that error appears in the above-identified patent and that said Letters Patent is hereby corrected as shown below:

Title Page, [57] ABSTRACT, line 2, formula (I);

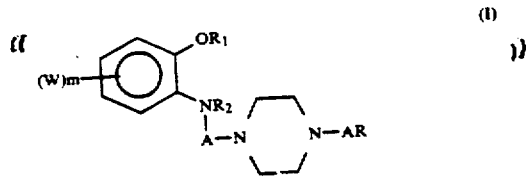

should read

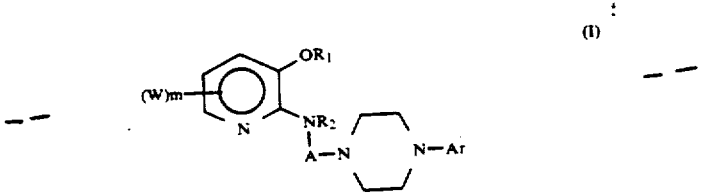

Signed and Sealed this

Twenty-second Day of November, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,084,456
DATED : January 28, 1992
INVENTOR(S) : Gerald Guillaumet, Christine Flouzat, Jacqueline Bonnet It is certified that error appears in the above-indentified patent and that said Letters Patent is hereby corrected as shown below:

Title page, item [75] Inventors: "Gerald Guillaumet, Christine Flouzat; Jacqueline Bonnet, all of Orleans, France:" should read --Gerald Guillaumet, Christine Flouzat; both of Orleans; Jacqueline Bonnet; Paris, France--.

Signed and Sealed this

Twenty-eight Day of March, 1995

Attest:

BRUCE LEHMAN

Attesting Officer     Commissioner of Patents and Trademarks